US006482425B1

(12) United States Patent
Huet et al.

(10) Patent No.: US 6,482,425 B1
(45) Date of Patent: Nov. 19, 2002

(54) PARASITICIDAL COMBINATION

(75) Inventors: Anne-Marie Huet, Toulouse (FR); Bruno Julia, Toulouse (FR); Jean-Pierre Etchegaray, Toulouse (FR); André Weil, Cugnaux (FR); Philippe Jeannin, Tournefeuille (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/271,470

(22) Filed: Mar. 17, 1999

Related U.S. Application Data

(63) Continuation-in-part of application No. PCT/FR97/01548, filed on Sep. 15, 1997.

(30) Foreign Application Priority Data

Sep. 19, 1996 (FR) ............................................ 96 11446

(51) Int. Cl.$^7$ ........................ A01N 25/32; A01N 43/90; A01N 31/08
(52) U.S. Cl. ....................... 424/406; 424/405; 424/407; 424/78.02; 514/30; 514/407
(58) Field of Search ........................ 424/405, 484–502, 424/406, 407, 78.02, 78.07; 514/30, 341, 407, 460, 782

(56) References Cited

U.S. PATENT DOCUMENTS

| | | | | |
|---|---|---|---|---|
| 4,468,390 A | * | 8/1984 | Gitano | ........................ 424/232 |
| 5,360,910 A | | 11/1994 | Huang et al. | ................ 546/279 |
| 5,586,843 A | * | 12/1996 | Steiter et al. | ................ 514/341 |
| 5,981,500 A | * | 11/1999 | Bimol et al. | ................... 574/30 |
| 6,054,140 A | * | 4/2000 | Lambern | .................... 424/405 |

FOREIGN PATENT DOCUMENTS

| | | |
|---|---|---|
| EP | 0295117 A1 | 12/1988 |
| EP | 0500209 A1 | 8/1992 |
| EP | 0679650 A1 | 11/1995 |
| FR | 2 713 889 A | 6/1995 |
| WO | WO 96 16543 A | 6/1996 |
| WO | WO 00/30449 | 6/2000 |

OTHER PUBLICATIONS

Postal et al Veteinary Dermatology *Fipronil* vol. 6, #3 pp. 153–158 '95.*
Aroeu et al Australian Vet. Phacthoner vol. 26 #3 pp. 155 '96.*
Database CABA STN–International STN–accession No. 95:202002, J.M. Postal, , "Efficacy of 0.25 Fipronil Based Formulation Spray In The Treatment and Prevention of Flea Infestations of Dogs and Cats", XP002028860 voir abrege & Professione Veterinaria, No. 1, 1995, pp. 17–18.
Research Disclosure, "Extended Efficacy Spectrum of Azole Pesticides" No. 380, Dec. 1, 1995, Havant GB, p. 802, XP00549823 voir le document en entier.
Database WPI, Section Ch, Week 9240, Derwent Publications Ltd., , London, GB. Class CO2, AN 92–327692 (Aug. 24, 1992) XP 002028892 & JP 04 235 104 A (Mitsubishi Kasei Corp), Aug. 24, 1992. voir abrege.
R. Atwell et al., The Effects of Fipronil on IxOdes Holocyclus on Dogs in Northern NSW, Australian Veterinary Practitioner, vol. 26, No. 3, Sep. 3, 1996, p. 155 XP 000647073, voir le document en entier.
P.R. Cooper, et al., "Use of Fipronil To Eliminate Recurrent Infestation By Trichodectes Canis In a Pack of Bloodhounds", The Veterinary Record, vol. 139 (Sep. 1996) p. 95.
Database CABA, STN–International, STN–accession No. 95:202003, C. Genchi, et al., "Efficacy of Fipronil In A Spray Formulation", (Frontline RM) in Treating Flea and Tick Infestation On Dogs XP 002028859, voir abrege & Professione Veterinaria No. 1, (suppl.), 1995, pp. 19–22.

* cited by examiner

*Primary Examiner*—Neil S. Levy
(74) *Attorney, Agent, or Firm*—Frommer Lawrence & Haug LLP; William S. Frommer; Thomas J. Kowalski

(57) ABSTRACT

The invention concerns a method and a composition against parasites and particularly ectoparasites and, preferably also endoparasites of small mammals and in particular dogs and cats. The composition contains a compound (A) of formula (I) and a compound (B) consisting of an endectoparasiticide of the macrocylic lactone type.

30 Claims, No Drawings

PARASITICIDAL COMBINATION

This is a continuation-in-part of copending International Application PCT/FR97/01548 having an international filing date of Sep. 15, 1997, and designating the U.S. and claiming priority from French Application No. 96/11446, filed Sep. 19, 1996. Reference is also made to: U.S. applications Ser. No. 719,942 U.S. Pat. No. 6,395,765, filed Sep. 25, 1996, (now U.S. Pat. Np. 6,395,765), Ser. No. 692,430, filed Aug. 5, 1996 (now abandoned), Ser. No. 863,182, filed May 27, 1997 (now U.S. Pat. No. 5,885,607), U.S. Pat No. 692,113, filed Aug. 5, 1996 (now abandoned), Ser. No. 863,392, filed May. 27, 1997 (now U.S. Pat. No. 6,096,329), and 08/891,047, filed Jul. 10, 1997(now U.S. Pat. No. 6,162,820); French Application No 97 03709, filed Mar. 26, 1997; and PCT/FR98/00601. All of the above-mentioned applications, as well as all documents cited herein and documents referenced or cited in documents cited herein, are hereby incorporated herein by reference.

The present invention relates to an improvement to methods for combating animal parasites, namely parasites of small mammals and of birds and in particular ectoparasitical insects and endoparasites, in particular filariae and worms.

It also relates to a new composition for this use, on the basis of a combination in which already known parasiticides are synergically combined. Finally, it relates to the use of such already known parasiticides in the preparation of a composition for combating parasites and in particular the abovementioned combinations of parasites.

A new family of insecticides based on 1-N-phenylpyrazoles has been described in Patents EP-A-295,217 and EP-A-352,944. The compounds of the families defined in these patents are extremely active and one of these compounds, 1-[2,6-Cl$_2$-4-CF$_3$phenyl]-3-CN-4-[SO-CF$_3$]-5-NH$_2$pyrazole, the common name of which is fipronil, has proved to be particularly effective, not only against crop parasites but also against ectoparasites of mammals and in particular, but not exclusively, fleas and ticks.

Endectocidal compounds exhibiting a degree of activity against endoparasites and comprising avermectins and their derivatives and related products, such as ivermectin, are also known. Such substances are, for example, described in U.S. Pat. Nos. 3,950,360 and 4,199,569.

Provision has often been made to combine parasiticides with the aim of broadening the antiparasitical spectrum and the combination of the abovementioned 1-N-phenylpyrazole derivatives with avermectins, ivermectins and milbemycin had already been mentioned, among many others, without, all the same, determining the specific advantage which such a combination might have, taking into account the numerous and complex host-parasite interactions.

Patent Application AU-A-16 427/95 mentions the combination of a substituted 1-N-pyrazole derivative of this type with avermectins, ivermectin or moxidectin, among a very large number of insecticides or parasiticides of various types, including fipronil moreover, without, however, giving information on a composition comprising such a combination and without establishing a distinction regarding the targets susceptible to being targeted by specific combinations, among the innumerable parasites which can potentially be attacked.

Apart from a very general teaching, the prior art thus does not make it possible to distinguish, in each specific case, the animals and the parasites for which a specific combination might be useful or the form of a composition containing such a combination.

Moreover, the prior art is silent with respect to the presentations, dosages, posologies and administration routes of combinations of these parasiticides, the sites, methods of effect, duration of effect and targets of which are very different.

The invention intends in particular to improve methods for combating parasites of small mammals, and in particular cats and dogs, with the aim of ridding these animals of all the parasites commonly encountered.

The invention intends in particular to provide for effective and lasting destruction of ectoparasites, such as fleas and ticks and possibly itch mites and lice, and of endoparasites, such as filariae, in particular dirofilariae, and roundworms of the digestive tract, in cats and dogs.

The following are in particular targeted among roundworms or nematodes: ascarids (in particular Toxocara canis), ancylostoma species (in particular Ancylostoma caninum) and Echinococcus and Trichuris species, in particular Trichuris vulpis.

A particular object of the invention is to use already known parasiticides to prepare a composition which is extremely active against fleas and, if appropriate, against ticks.

Another object of the invention is to produce such compositions which make it possible, inter alia, effectively to combat certain endoparasites and in particular filariae and/or roundworms.

The very high effectiveness of the method and of the composition according to the invention implies not only high instantaneous effectiveness but also an effectiveness of very long duration after the treatment of the animal.

Flea within the meaning of the present invention is understood to mean in particular the Ctenocephalides species, in particular felis and canis.

Filaria is understood to mean in particular Dirofilaria immitis.

Toxocara canis, Ancylostoma caninum and Trichuris vulpis are understood in particular among the other nematodes.

The subject of the invention is a method for combating parasites and in particular ectoparasites and, preferably, also endoparasites of small mammals and in particular dogs and cats, characterized in that the animal is treated, preventively or curatively, by administration in effectively parasiticidal doses and proportions, on the one hand, of at least one compound (A) belonging to the formula (I)

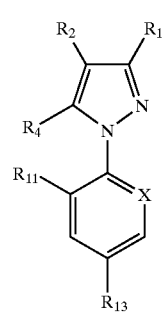

(I)

in which:
  $R_1$ is a halogen atom, CN or methyl;
  $R_2$ is S(O)$_n$R$_3$ or 4,5-dicyanoimidazol-2-yl or haloalkyl;
  $R_3$ is alkyl or haloalkyl;
  $R_4$ represents a hydrogen or halogen atom or an NR$_5$R$_6$, S(O)$_m$R$_7$, C(O)R$_7$ or C(O)OR$_7$, alkyl, haloalkyl or OR$_8$ radical or an —N=C (R$_9$) (R$_{10}$) radical;
  $R_5$ and $R_6$ independently represent a hydrogen atom or an alkyl, haloalkyl, C(O)alkyl, S(O)$_r$CF$_3$ or alkoxycarbonyl radical or $R_5$ and $R_6$ can together form a divalent alkylene radical which can be interrupted by one or two divalent heteroatoms, such as oxygen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted by one or more halogen atoms or groups such as OH, —O-alkyl, —S-alkyl, cyano or alkyl;

$R_{11}$ and $R_{12}$ represent, independently of one another, a hydrogen or halogen atom and optionally CN or $NO_2$, but H or halogen being preferred;

$R_{13}$ represents a halogen atom or a haloalkyl, haloalkoxy, $S(O)_qCF_3$ or $SF_5$ group;

m, n, q and r represent, independently of one another, an integer equal to 0, 1 or 2;

X represents a trivalent nitrogen atom or a C-$R_{12}$ radical, the three other valencies of the carbon atom forming part of the aromatic ring;

with the proviso that, when $R_1$ is methyl, then either $R_3$ is haloalkyl, $R_4$ is $NH_2$, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl and, on the other hand, of at least one compound (B) formed of an endectocidal parasiticide of macrocyclic lactone type.

The parasiticide (B) is preferably selected from the group formed by avermectins, ivermectin, abamectin, doramectin, moxidectin, milbemycins and the derivatives of these compounds.

The structure, the characteristics and the processes for the manufacture of the compounds of type (B) are well known to a person skilled in the art and reference can be made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216–4221. For doramectin, "Veterinary Parasitology", vol. 49, No. 1, July 1993, 5–15 may in particular be consulted. For milbemycins, reference may be made, inter alia, to Davies H. G. et al., 1986, "Avermectins and Milbemycins", Nat. Prod. Rep., 3, 87–121, Mrozik H. et al., 1983, Synthesis of Milbemycins from Avermectins, Tetrahedron Lett., 24, 5333–5336, and U.S. Pat. No. 4,134,973.

Compounds (B) can be either natural products or are semi-synthetic derivatives thereof. The structure of at least certain compounds (B) are closely related, e.g., by sharing a complex 16-membered macrocyclic lactone ring. The natural product avermectins are disclosed in U.S. Pat. No. 4,310,519 to Albers-Schonberg, et al., and the 22, 23-dihydro avermectin compounds are disclosed in Chabala, et al., U.S. Pat. No. 4,199,569. Mention is also made of Kitano, U.S. Pat. No. 4,468,390, Beuvry et al., U.S. Pat. No. 5,824,653, European Patent Application 0 007 812 A1, published Jun. 2, 1980, U.K. Patent Specification 1 390 336, published Apr. 9, 1975, European Patent Application 0 002 916 A2, and Ancare New Zealand Patent No. 237 086, inter alia. Naturally occurring milbemycins are described in Aoki et al., U.S. Pat. No. 3,950,360 as well as in the various references cited in "The Merck Index" $12^{th}$ ed., S. Budavari, Ed., Merck & Co., Inc. Whitehouse Station, New Jersey (1996). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148.

The alkyl radicals of the definition of the compounds (A) of the formula (I) generally comprise from 1 to 6 carbon atoms. The ring formed by the divalent alkylene radical representing $R_5$ and $R_6$ and the nitrogen atom to which $R_5$ and $R_6$ are attached is generally a 5-, 6- or 7-membered ring.

A preferred class of compounds (A) of formula (I) comprises the compounds such that $R_1$ is CN, $R_3$ is haloalkyl, $R_4$ is $NH_2$, $R_{11}$ and $R_{12}$ are, independently of one another, a halogen atom and $R_{13}$ is haloalkyl. Preferably still, X is C—$R_{12}$.

A compound (A) of formula (I) which is very particularly preferred in the invention is 1-[2,6-$Cl_2$-4-$CF_3$phenyl]-3-CN-4-[SO—$CF_3$]-5-$NH_2$pyrazole, hereinafter known as compound A, the common name of which is fipronil.

More generally, compounds (A) are pyrazoles such as phenylpyrazoles and N-arylpyrazoles, and reference is made to, for example, U.S. Pat. No. 5,567,429, U.S. Pat. No. 5,122,530, EP 295,117, and EP 846686 A1 (or Banks GB 9625045, filed Nov. 30, 1996 also believed to be equivalent to U.S. Ser. No. 309,229, filed Nov. 17, 1997). (e.g., 1-pyridyl imidazole compounds, an N-aryldiazole compounds, and a phenylpyrazole compounds).

Compounds (A) of formula (I) can be prepared according to one or other of the processes described in Patent Applications WO 87/3781, 93/6089 and 94/21606 or European Patent Application 295,117 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

The two types of compounds can be administered concomitantly and preferably simultaneously in the form of a single composition.

Administration can be intermittent in time and, in this case, it is preferable for the treatment according to the invention to be carried out monthly on dogs and on cats.

Frequencies of less than a monthly frequency are also possible, for example bimonthly or quarterly or even more. In other words, a method for permanently combating in an environment in which the animal is subjected to strong parasitic pressure is characterized by an administration at a frequency far below a daily administration.

However, administration can also be continuous using means, known in themselves, which make possible slow liberation or release of the compounds combined in the treatment. Mention may in particular be made of microspheres based on polylactic acid polymer or on polylactic-glycolic acid copolymer.

In this case, it will be preferable to administer to the animal, by a route providing good systemic distribution, a mixture of two controlled-release formulations, one containing the compound (A) and the other the compound (B).

The compounds for the treatment can be administered by a systemic route, for example an oral or parenteral route.

Administration is preferably carried out topically, on the skin or the coat of the animal.

Preferably, in the case of topical administration, a single composition containing the compounds (A) and (B) in a substantially liquid vehicle and in a form which makes possible a single application, or an application repeated a small number of times, will be administered to the animal over a highly localized region of the animal, preferably between the two shoulders (formulation of spot-on type). It has been possible to observe, remarkably, that such a formulation makes it possible to obtain high effectiveness in the companion animal both against the targeted ectoparasites and the targeted endoparasites.

The treatment is preferably carried out so as to administer to the animal, on a single occasion, a dose containing between 0.001 and 100 mg/kg of derivative (A) and containing between 0.1 and 1000 μg/kg of compound of type (B), in particular in the case of a direct topical administration.

The amount of compound (A) for animals which are small in size is preferably greater than 0.01 mg and in a particularly preferred way between 1 and 50 mg/kg of weight of animal.

For administration by the oral or parenteral route, the doses can comprise the compounds (A) and (B) in the same ranges mentioned above.

In the case where the compounds of the treatment according to the invention are administered continuously, for example from systemic-distribution release means, it is preferable for the release rate to be of the order of 0.001 to 0.5 mg, preferably of 0.05 to 0.1 mg/kg per day for the compound (A) and of 0.1 to 200 μg/kg per day for the compound (B).

In the case of administration by an oral or parenteral systemic route, it is preferable for the dose to result in a blood concentration greater than or equal to 1 ng, for example 1 to 50 ng/ml for the compound (A).

To this end, it may be preferable to use controlled-release formulations. However, due to the persistence of the activity of fipronil and of the derivatives of type (B), it may be preferable for reasons of simplicity to carry out systemic administration using conventional vehicles.

The object of this method is non-therapeutic and relates in particular to the cleaning of the coats and of the skin of animals by removal of the parasites which are present and of their waste and excreta. The animals treated thus exhibit a coat which is more pleasing to the eye and more pleasant to the touch.

The invention also relates to such a method with a therapeutic aim intended for the treatment and prevention of parasitoses having pathogenic consequences.

Another subject of the invention is a composition, in particular for combating fleas in small mammals, in particular dogs and cats, characterized in that it contains, on the one hand, at least one compound (A) of formula (I). as defined above and, on the other hand, at least one endectocidal compound (B), in amounts and proportions having a parasiticidal effectiveness for fleas and worms, in a vehicle acceptable for the animal.

The preferred class of compounds of formula (I) is that which has been defined above.

A compound of formula (I) which is very particularly preferred in the invention is 1-[2,6-Cl$_2$-4-CF$_3$phenyl]-3-CN-4-[SO—CF$_3$]-5-NH$_2$pyrazole.

Among the compounds of type (B), for small animals, a compound selected from the group formed by ivermectin and milbemycin is preferred.

The effective amount in a dose is, for the compound (A), preferably between 0.001, preferentially 0.1, and 100 mg and in a particularly preferred way from 1 to 50 mg/kg of weight of animal, the higher amounts being provided for very prolonged release in or on the body of the animal.

The effective amount of compounds (B) in a dose is preferably between 0.1 μg, preferentially 1 μg, and 1 mg and in a particularly preferred way from 5 to 200 μg/kg of weight of animal.

The proportions, by weight, of compounds of formula (I) and of compounds (B) are preferably between 5/1 and 10,000/1.

The vehicle can be simple or complex and it is suited to the route and to the method of administration chosen.

Thus, the composition according to the invention can be provided in the topical form, in particular in the form of a solution, suspension, microemulsion or emulsion to be poured or spread over the animal (solution of pour-on type), of a more concentrated solution, suspension, microemulsion or emulsion for intermittent application to a spot-on the animal, generally between the two shoulders (solution of spot-on type), or of an oil, cream, ointment or any other fluid formulation for topical administration.

The formulation which is particularly preferred, and which exhibits a particularly surprising effectiveness, in particular with respect to dogs and cats and small mammals generally, is the concentrated suspension or solution for intermittent application (solution of so-called spot-on type).

Such a preparation exhibits, in a particularly preferred way, the compounds (A) and (B) in a vehicle for cutaneous application containing an organic solvent and, preferably, an organic cosolvent and/or a crystallization inhibitor.

The compound (A) of formula (I) can advantageously be present in this formulation in a proportion of 1 to 20%, preferably of 5 to 15% (percentages as weight by volume =W/V).

The crystallization inhibitor can in particular be present in a proportion of 1 to 20% (W/V), preferably of 5 to 15%, this inhibitor preferably corresponding to the test according to which: 0.3 ml of a solution comprising 10% (W/V) of the compound of formula (I) in the solvent defined under c) below, as well as 10% of this inhibitor, are deposited on a glass slide at 20° C. for 24 hours, following which few or no crystals, in particular less than 10 crystals, preferably 0 crystals, are observed with the naked eye on the glass slide.

The organic solvent will preferably have a dielectric constant of between 10 and 35, preferably between 20 and 30, the content of this solvent in the overall composition preferably representing the remainder to 100% of the composition.

The organic cosolvent will preferably have a boiling point of less than 100° C., preferably of less than 80° C., and will have a dielectric constant of between 10 and 40, preferably between 20 and 30; this cosolvent can advantageously be present in the composition according to a weight/weight (W/W) ratio with respect to the solvent of between 1/15 and 1/2; the cosolvent is volatile in order to act in particular as drying promoter and is miscible with water and/or with the solvent.

Although this is not preferred, the composition can optionally comprise water, in particular in a proportion of 0 to 30% (volume by volume V/V), in particular of 0 to 5%.

The composition can also comprise an antioxidizing agent intended to inhibit oxidation in air, this agent being in particular present in a proportion of 0.005 to 1% (W/V), preferably of 0.01 to 0.05%.

Use can in particular be made, as organic solvents, of the following: acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as $C_9$–$C_{10}$ caprylic/capric triglyceride (Estasan or Miglyol 812), oleic acid or propylene glycol.

An organic solvent can be selected from the group consisting of acetone, benzyl alcohol, butyl diglycol, dipropylene glycol n-butyl ether, ethanol, isopropanol, methanol, ethylene glycol monoethyl ether, ethylene glycol monomethyl ether, dipropylene glycol monomethyl ether, propylene glycol, diethylene glycol monoethyl ether, ethylene glycol, and a mixture of at least two of these solvents.

Mention may in particular be made, as crystallization inhibitor which can be used in the invention, of:

- polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others,
- anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil,
- cationic surfactants, such as water-soluble quaternary ammonium salts of formula $N^+R'R''R'''R''''$ $Y^-$, in which the R radicals are optionally hydroxylated hydrocarbon radicals and $Y^-$ is an anion of a strong acid, such as halide, sulphate and sulphonate anions; cetyltrimethylammonium bromide is one of the cationic surfactants which can be used,
- amine salts of formula $N^{30}$ $R'R''R'''$, in which the R radicals are optionally hydroxylated hydrocarbon radicals; octadecylamine hydrochloride is one of the cationic surfactants which can be used,
- non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide,
- amphoteric surfactants, such as substituted lauryl compounds of betaine,
- or preferably a mixture of at least two of them.

In a particularly preferred way, use will be made of a crystallization inhibitor pair, namely the combination of a film-forming agent of polymeric type and of a surface-active agent. These agents will be selected in particular from the compounds mentioned above as crystallization inhibitor.

Mention may be made, among the particularly advantageous film-forming agents of polymeric type, of:

- the various grades of polyvinylpyrrolidone,
- polyvinyl alcohols, and
- copolymers of vinyl acetate and of vinylpyrrolidone.

For the surface-active agents, mention will very particularly be made of non-ionic surfactants, preferably polyoxyethylenated esters of sorbitan and in particular the various grades of Polysorbate, for example Polysorbate 80.

The film-forming agent and the surface-active agent can in particular be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the fur, that is to say without a tendency towards sticking or towards a sticky appearance, despite the high concentration of active material.

Mention may in particular be made, as cosolvent which is a promoter of drying, of: absolute ethanol, isopropanol (2-propanol) or methanol.

Use is in particular made, as antioxidizing agent, of conventional agents, such as: butylated hydroxyanisole, butylated hydroxytoluene, ascorbic acid, sodium metabisulphite, propyl gallate, sodium thiosulphate or a mixture of not more than two of them.

These concentrated compositions are generally prepared by simple mixing of the constituents as defined above; advantageously, the starting point is to mix the active material in the main solvent and then the other ingredients or adjuvants are added.

The volume applied can be of the order of 0.3 to 1 ml, preferably of the order of 0.5 ml, for cats and of the order of 0.3 to 3 ml for dogs, depending on the weight of the animal.

Microemulsions are also well suited to intermittent topical application.

Microemulsions are quaternary systems comprising an aqueous phase, an oily phase, a surfactant and a cosurfactant. They are translucent and isotropic liquids.

They are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. It will preferably concern triglycerides and more particularly medium-chain triglycerides, for example $C_8$–$C_{10}$ caprylic/capric triglyceride. The oily phase will represent in particular from 2 to 15%, more particularly from 7 to 10%, preferably from 8 to 9%, V/V of the microemulsion.

The aqueous phase can in particular be selected from water or glycol derivatives in general, such as propylene glycol, glycol ethers, polyethylene glycols or glycerol. Preference will be given to propylene glycol, diethylene glycol monoethyl ether and dipropylene glycol monoethyl ether.

It will amount to a proportion in particular of 1 to 4% V/V in the microemulsion.

The surfactant will preferably be selected from diethylene glycol monoethyl ether, dipropylene glycol monomethyl ether, polyglycolysed $C_8$–$C_{10}$ glycerides or polyglyceryl-6 dioleate.

The cosurfactant will preferably be selected from short-chain alcohols, such as ethanol and propanol. It can also be one of the compounds mentioned as surfactant.

Some compounds are common to the three components: aqueous phase, surfactant and cosurfactant. However, it will be arranged to use different compounds for each component of the same formulation.

The cosurfactant to surfactant ratio will preferably be from 1/7 to 1/2. There will preferably be from 25 to 75% V/V of surfactant and from 10 to 55% V/V of cosurfactant in the microemulsion.

One or more crystallization inhibitors defined above can advantageously be added to the microemulsion. It will preferably be a crystallization inhibitor pair as described above, in particular Polysorbate 80 and polyvidone (polyvinylpyrrolidone), such as Kollidon 17 PF from BASF, Germany. The amounts will be the same as for the cutaneous spot-on solution, for example approximately 5% N/V of each of the compounds of the crystallization inhibitor pair.

The active compounds (A) and (B) can be present in the proportions shown for the cutaneous solution of spot-on type.

For administration by the oral route, use can be made of all the usual formulations, such as solutions, microemulsions, emulsions or suspensions, to be mixed with foods, or appetent formulations, such as pellets or tablets, powders, hard gelatin capsules or others.

The preferred compound (A) is, in the case of a composition for oral absorption, the derivative of formula (II):

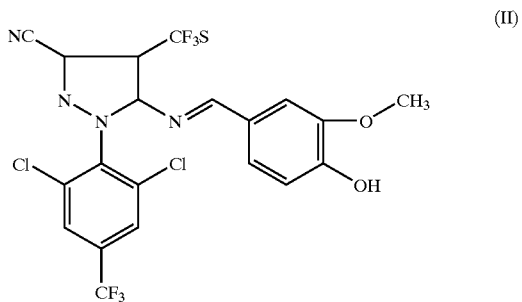

For parenteral administration, preference will be given to a formulation in solution injectable, preferably, by the subcutaneous route, preferably with an oily adjuvant, for example a mixture of organic solvents and of vegetable oils.

The composition for parenteral administration can also be produced in particulate form, in particular in the form of nanoparticles and nanocapsules, microparticles, microcapsules or liposomes or alternatively in the form of implants. These particles can be produced, in particular, from poly-lactic or polylactic-glycolic acid polymer, for example in water or in a vegetable oil or a medium-chain triglyceride.

The compositions according to the invention have proved to be extremely effective in the very long lasting treatment of fleas of mammals and in particular of small mammals such as dogs and cats.

They also exhibit a degree of effectiveness against other parasitic insects and in particular ticks and flies and it is understood that it is possible to extend the application of the composition according to the invention to the treatment of ectoparasites, indeed of endoparasites, for which parasites the composition proves to exhibit a true usefulness capable of being obtained in practice, according to the criteria of the veterinary art, in particular against major endoparasites, in particular the dirofilariasis parasite and/or roundworms.

Thus, for example, a composition based on fipronil and on milbemectin can also be used, in particular against filariae and roundworms.

Another subject of the invention is the use of at least one compound of formula (I) and of at least one compound of type (B), as defined above, in the preparation of a composition as defined above.

Other advantages and characteristics of the invention will become apparent on reading the following description, given by way of non-limiting example.

EXAMPLE 1

Preparation of a Formulation for Oral Absorption by Dogs.

A mixture of fipronil and of ivermectin is produced and packaged in hard gelatin capsules of conventional type. One hard gelatin capsule is designed to treat a dog weighing 10 kg. It contains 200 mg of fipronil and 2.5 mg of ivermectin.

The dogs are treated orally and experimentally infested with 100 fleas and 50 ticks on D-1, D7 and weekly thereafter until 42 days after treatment. The results show the effectiveness of this treatment.

The ivermectin can be replaced in the hard gelatin capsules by another endectocide (B), for example milbemycin in a proportion of 500 µg/kg of animal weight.

Likewise, fipronil can be replaced by vaniliprole, preferably by an equal dose thereof.

EXAMPLE 2

Preparation of a Concentrated Solution for Intermittent Application (spot-on).

A concentrated solution for cutaneous application is prepared which contains, as weight by volume of solution, 10% of fipronil and 0.25% of ivermectin. The administration volume is 1 ml per 10 kg of animal weight. The composition is as follows, as weight/volume:

fipronil: 10% ivermectin 0.25%

Polyvinylpyrrolidone (Kollidon 17 PF): 5%

Polysorbate 80 (Tween 80): 5% ethanol: 10%

Transcutol: q.s for 100%.

EXAMPLE 3

Preparation of a Concentrated Microemulsion for Intermittent Application (spot-on).

The ingredients used are as follows:

oily phase: $C_{8-C10}$ caprylic/capric triglyceride (Estasan)

aqueous phase: propylene glycol surfactant: diethylene glycol monoethyl ether (Transcutol)

cosurfactant: ethanol or 2-propanol crystallization inhibitor pair: Polysorbate 80 (Tween 80) and polyvinylpyrrolidone (Kollidon 17 PF).

A composition example contains:

fipronil: 10 g ivermectin: 0.5 g

Estasan: 8.5 ml

Transcutol: 60 ml ethanol: 15 ml

Kollidon 17 PF: 5 g

Tween 80: 5 g propylene glycol: q.s. for 100 ml.

In the formulation described, the Transcutol acts as the surfactant (SA) and the ethanol or 2-propanol acts as cosurfactant (Co-SA). They make it possible to obtain, from a mixture of medium-chain triglycerides (Estasan) which is immiscible with propylene glycol, an isotropic transparent micro-emulsion. The crystallization inhibitor pair will be added once the microemulsion has been formed.

EXAMPLE 4

Five dogs weighing 12 kg, deprived of food, receive the application of 1 ml of composition according to Example 2 or 3, i.e. 100 mg of fipronil and 2.5 mg of ivermectin, by localized cutaneous application between the two shoulders.

The measurements carried out on the plasma of the animals show the production of an ivermectin peak of 1000 to 1500 to 2000 pg/ml.

A monthly or even bimonthly treatment of dogs makes possible complete control of fleas, ticks and dirofilariasis parasites.

EXAMPLE 5

Preparation of an Injectable Composition.

A group of dogs is treated subcutaneously using a solution containing 3.3% M/V of fipronil and 0.08% of ivermectin in a mixture of organic solvents and of vegetable oil or of medium-chain triglyceride fipronil 3.3 g ivermectin 0.08 g Transcutol 15 ml Estasan q.s. for 100 ml.

Minimum effective plasma concentrations are obtained for a period of time of at least three months against fleas and ticks, and the dirofilariasis cycles are interrupted.

EXAMPLE 6

Dogs are treated subcutaneously with micro-spheres made of polylactic acid polymer or of polylactic-glycolic acid copolymer PLA 100 D.L., with a molecular weight of approximately 100,000, at 15% M/V in water or in a vegetable oil or in a medium-chain triglyceride, containing 3.3% M/V of fipronil and 0.08% M/V of ivermectin, in a proportion of 0.3 ml/kg.

Effective plasma concentrations of fipronil are obtained for a period of time of at least six to seven months against fleas and ticks.

What is claimed is:

1. A method for combating parasites of a cat or dog comprising localized cutaneous application to the cat or dog, between the shoulders, at a frequency not greater than monthly, of a spot-on composition, which comprises, in a veterinarily acceptable vehicle, an amount parasitically effective of at least one compound (A), and an amount parasitically effective of at least one compound (B), wherein:

compound (A) is an ectoparasiticide of the formula (I)

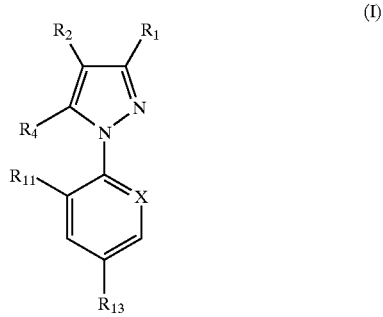

(I)

in which:

$R_1$ is CN;

$R_2$ is $S(O)_n R_3$;

$R_3$ haloalkyl;

$R_4$ represents $NH_2$;

$R_{11}$ represents halogen atom;

$R_{13}$ represents haloalkyl;

n represents an integer equal to 0, 1 or 2;

X represents a radical $C-R_{12}$;

$R_{12}$ represents a halogen atom;

and compound (B) is an endectocidal parasiticide of the macrocyclic class of compounds selected from the group consisting of avermectin, abamectin and doramectin; and, the vehicle is for a localized cutaneous application to the animal between the shoulders and contains an organic solvent, and organic cosolvent and/or a crystallization inhibitor wherein:

the crystallization inhibitor selected from the group consisting of polyvinylpyrrolidone, copolymers of vinyl acetate and vinylpyrrolidone, polyoxyethylenated sorbitan esters and mixtures thereof;

the organic solvent comprises acetone, ethyl acetate, methanol, ethanol, isopropanol, dimethylformamide, dichloromethane or diethylene glycol monoethyl ether; said solvent optionally supplemented by $C_8-C_{10}$ caprylic/capric triglyceride, oleic acid or propylene glycol or the organic solvent comprises dipropylene glycol monomethyl ether; and the organic cosolvent selected from the group consisting of ethanol, isopropanol, and methanol;

whereby there is a prolonged release of compound (A) in or on the body of the cat or dog and there is a measurable plasma level of compound (B) in the cat or dog.

2. The method of claim 1 wherein in the spot-on composition the compound (B) is an avermectin or a doramectin, and the vehicle comprises isopropanol and dipropylene glycol monomethyl ether.

3. The method of claim 1 wherein in the spot-on composition the compound (B) is an abamectin or a doramectin.

4. The method of claim 1 wherein in the spot-on composition the compound (B) is an avermectin.

5. The method of claim 4 wherein in the spot-on composition the compound (B) is ivermectin.

6. The method of claim 1 wherein in compound (A) the haloalkyl radicals contain from 1 to 6 carbon atoms.

7. The method of claim 1 wherein in the spot-on composition compound (A) is 1-[4-$CF_3$ 2,6-$Cl_2$ phenyl] 3-cyano 4-[$CF_3$—SO] 5-$NH_2$ pyrazole.

8. The method of claim 3 wherein in the spot-on composition compound (B) is an abamectin.

9. The method of claim 3 wherein in the spot-on composition compound (B) is a doramectin.

10. The method of claim 7 wherein in the spot-on composition compound (B) is an avermectin.

11. The method of claim 10 wherein in the spot-on composition compound (B) is ivermectin.

12. The method according to any one of claim 1, 2, 3, 4, 5, 6, 7, 10 or 11 wherein compound (A) is present in the spot-on composition in an amount up to 100 mg/kg of weight of animal and compound (B) is present in the spot-on composition in an amount up to 1 mg/kg of weight of animal.

13. The method of claim 12 wherein compound (A) is present in the spot-on composition in an amount of from 0.1 to 100 mg/kg of weight of animal.

14. The method of claim 13 wherein compound (B) is present in the spot-on composition in an amount of from 1 µg to 1 mg/kg of weight of animal.

15. The method according to any one of claim 1, 2, 3, 4, 5, 6, 7, 10 or 11 wherein compound (A) is present in the spot-on composition in an amount between 1 and 50 mg/kg of weight of animal.

16. The method according to any one of claim 1, 2, 3, 4, 5, 6, 7, 10 or 11 wherein compound (B) is present in the spot-on composition in an amount between 5 and 200 µg/kg of weight of animal.

17. The method according to claim 16 wherein compound (A) is present in the spot-on composition in an amount between 1 and 50 mg/kg of weight of animal.

18. The method according to any on of claim 1, 2, 3, 4, 5, 6, 7, 10 or 11 wherein the proportion, by weight of compound (A) to compound (B) in the spot-on composition is between 5/1 and 10,000/1.

19. The method of claim 1 wherein the crystallization inhibitor in the spot-on composition is a crystallization inhibitor pair.

20. The method according to any one of claim 1, 3, 4, 5, 6, 7, 10 or 11 wherein the organic solvent in the spot-on composition is diethylene glycol monoethyl ether.

21. The method according to any one of claim 1, 3, 4, 5, 6, 7, 10 or 11 wherein the organic cosolvent in the spot-on composition is ethanol or isopropanol.

22. The method of claim 1 or 2 wherein there is a weight/weight ratio of the cosolvent/solvent in the spot-on composition and the weight/weight ratio of the cosolvent/solvent is between 1/15 and 1/2.

23. The method of claim 1 wherein the spot-on composition further comprises water in an amount of less than 30% (volume/volume).

24. The method of claim 1 wherein the spot-on composition does not contain water.

25. The method of claim 1 wherein the crystallization inhibitor is present in the spot-on composition in an amount of 5 to 15% (weight/volume).

26. The method of claim 1 wherein the spot-on composition further comprises an antioxidant.

27. The method of claim 26 wherein the antioxidant is present in the spot-on composition in an amount of 0.005 to 1% weight/volume and is selected form the group consisting of butylated hydroxyanisole, butylated hydroxytoluene, ascorbic acid, sodium metabisulphite, propyl gallate, and sodium thiosulphate.

28. The method of claim 1 wherein the frequency is bimonthly or quarterly.

29. The method of claim 1 wherein the application is to a cat.

30. The method of claim 1 wherein the application is to a dog.

* * * * *

UNITED STATES PATENT AND TRADEMARK OFFICE
CERTIFICATE OF CORRECTION

PATENT NO.     : 6,482,425 B1
DATED          : November 19, 2002
INVENTOR(S)    : Anne-Marie Huet et al.

It is certified that error appears in the above-identified patent and that said Letters Patent is hereby corrected as shown below:

<u>Title page,</u>
Item [73], change, "Lyons" to -- Lyon --.

<u>Column 13,</u>
Line 10, change "on" to -- one --.

Signed and Sealed this

Fourth Day of March, 2003

JAMES E. ROGAN
*Director of the United States Patent and Trademark Office*